(12) United States Patent
Henrichs et al.

(10) Patent No.: US 6,424,857 B1
(45) Date of Patent: Jul. 23, 2002

(54) USE OF ACOUSTO-OPTICAL AND SONOLUMINESCENE CONTRAST AGENTS

(75) Inventors: Paul Mark Henrichs, Houston, TX (US); Henry Raphael Wolfe, Glenmore, PA (US)

(73) Assignee: Amersham Health AS, Oslo (NO)

( * ) Notice: Subject to any disclaimer, the term of this patent is extended or adjusted under 35 U.S.C. 154(b) by 0 days.

(21) Appl. No.: 09/458,007

(22) Filed: Dec. 10, 1999

Related U.S. Application Data

(63) Continuation of application No. PCT/GB98/01438, filed on Jun. 15, 1998.
(60) Provisional application No. 60/050,115, filed on Jun. 18, 1997.

(30) Foreign Application Priority Data

Jun. 16, 1997 (GB) ................................................ 9712525

(51) Int. Cl.⁷ ................................................. A61B 7/06
(52) U.S. Cl. ........................ 600/431; 600/407; 600/437; 600/473; 424/9.6; 424/9.51; 424/9.61
(58) Field of Search ............................... 600/407, 431, 600/473, 476, 425, 437; 424/9.6, 9.51, 9.61; 250/458.1, 361 C

(56) References Cited

U.S. PATENT DOCUMENTS 4,948,975 A    8/1990  Erwin et al.
5,491,344 A  * 2/1996  Kenney et al. .......... 250/461.1
5,659,173 A  * 8/1997  Putterman et al. ...... 250/361 C

FOREIGN PATENT DOCUMENTS

WO           0 552 107 A     7/1993
WO        WO 96 23524 A      8/1996

OTHER PUBLICATIONS

Database Medline US National Library of Medicine (NLM), Karev I.D. et al., "Ultrasonic luminescence of blood plasma in the differential diagnosis of rectal cancer!. Ul'trazvukovoe svechenie plazmy krovi v differentsial'noi diagnostike raka priamoi kishki." XP002077622 1991.

\* cited by examiner

*Primary Examiner*—Ruth S. Smith
(74) *Attorney, Agent, or Firm*—Bacon & Thomas

(57) ABSTRACT

The invention relates inter alia to a method of generating information from an animate human or non-human animal body which method comprises: administering to said body a physiologically tolerable material capable of absorbing, scattering or emitting light at a wavelength in the range 300 to 1300 nm; subjecting at least a portion of said body to ultrasound irradiation; detecting light in the wavelength range 300 to 1300 nm from said portion of said body; and manipulating the detected light to generate said information.

4 Claims, No Drawings

USE OF ACOUSTO-OPTICAL AND SONOLUMINESCENE CONTRAST AGENTS

This application is a continuation of pending international application number PCT/GB98/01438 filed Jun. 15, 1998 (of which the entire disclosure of the pending, prior application is hereby incorporated by reference), which itself is a continuation-in-part of U.S. provisional application No. 60/050,115 filed Jun. 18, 1997, benefit of which is claimed under 35 USC 119(e).

This invention relates to a method of diagnostic imaging of a human or animal subject, in particular a method in which the image is generated from detected light generated by or characteristically affected by ultrasound irradiation of the subject.

Optical imaging, also called light imaging, is perhaps one of the oldest of medical tools for screening and diagnosis. However, even now, optical imaging is largely limited to body surfaces. The primary advances in optical imaging have served essentially only to expand the range of body surfaces accessible to optical imaging techniques. Thus for example endoscopic techniques have made it possible to image from within the gastrointestinal tract, the cardiovascular system, the bladder, the vagina and uterus as well as the external surface of almost any internal organ. However, the deep interior of most organs, several centimeters beneath the surface, remains almost inaccessible to optical imaging.

There are two primary difficulties associated with subsurface optical imaging. These arise from light absorption and light scattering.

Naturally occurring substances in the body strongly absorb most visible light before it has travelled through typical tissue to any significant extent. Thus by way of example the absorption coefficient for light of 515 nm wavelength by human liver is 18.9 cm$^{-1}$ which means that on average a photon at 515 nm travels only about 0.5 mm in the liver before it is absorbed.

Because the photon follows a non-linear path within the tissue as a result of scattering, the actual depth of penetration before absorption is less than the pathlength of 0.5 mm.

Fortunately there is a wavelength "window" at 600 to 1300 nm in the red to near infrared region in which light absorption by the body is relatively weak. Thus for liver and breast tissue the absorption coefficients for light of wavelength 635 nm are only 2.3 cm$^{-1}$ and 0.2 cm$^{-1}$ giving mean pathlengths before absorption for photons at 635 nm of about 4.3 mm and 50 mm respectively. At these wavelengths, bone and brain are also relatively transparent so that absorption alone is not a barrier to light imaging with red to near infrared light. Thus, the penetration depth of light at 635 nm is an order of magnitude greater than that of light at 515 nm.

Light scattering however remains a major obstacle to light imaging of subsurface structures. Thus while light of wavelengths 600 to 1300 nm may pass through tissues and organs, the scattering that occurs means that the information on subsurface structures that would be extractable from the detected transmitted or reflected light is largely lost and small or deeply buried structures are not detectable distinctly by eye. At 635 nm, the scattering coefficient for human breast tissue is 395 cm$^{-1}$ meaning that while on average a photon will travel several centimeters before being absorbed it is constantly diverted by scattering events which occur on average every 2 $\mu$m. In other tissues, the scattering may be less severe but it is still substantial. The typical photon will travel only 16 $\mu$m between scattering events in brain grey matter for example.

While light scattering in the body is random, it is also highly anisotropic—the paths of the photon before and after a scattering event are not on average highly divergent. This scattering type is typical of Mie scattering.

To take account of the anisotropy of scattering, the reduced scattering coefficient $\mu_s'$ is used in place of the simple scattering coefficient $\mu_s$ in certain mathematical models. $\mu_s'$ is related to $\mu_s$ by the equation $\mu_s' = \mu_s(1-g)$ where g is the average cosine of the angle between the photon's incoming and departing paths for scattering events. For human grey matter $\mu_s'$ is only 7.22 cm$^{-1}$ meaning that light travels about 0.1 mm before its direction of propagation is significantly altered. This means that even after passing through several centimeters of breast or other tissue a light beam may still have a significant component which is travelling in substantially the same direction as the incident light beam. This component is often referred to as the quasi-ballistic component and it is this component which is of particular utility in light imaging of subsurface structures.

Thus, since the flight path of the quasi-ballistic photons through tissue is shorter than the path of the more highly scattered photons, the diffuse component, it is possible to separate out the transmitted light into its quasi-ballistic and diffuse components. This may be done for example by using a pulsed light source and detecting the leading edges of the transmitted pulsed light.

Despite its technical difficulties, light imaging has important advantages over other medical imaging modalities in that it can provide functional information as well as spatial information about the body. Thus with suitable modification it may be used for example to measure pH, oxygen content, metal concentration, etc.

Acousto-optical imaging is a modified approach to light imaging in which focused ultrasound is used to isolate optical signals from the body. Several mechanisms of interaction are possible. In one of these the acoustic wave sets up moving regions of different pressure, density and refractive index that interact with the light in much the same way as a diffusion grating. The movement of the sound waves moreover induces a Doppler shift of the sound frequency into the light frequency making it possible to identify that portion of the light that has actually interacted with the sound wave. Thus the light that has passed through the focused ultrasound region may be separated from other components of the detected light because it is shifted in frequency and wavelength. Acousto-optic imaging is described for example in U.S. Pat. No. 5,171,298, and by Wang et al. *Optics Letters* 20: 629–631 (1995), Wang et al. *Proc. Opt. Soc. Amer.* ATuB3-1: 166–168 (1996), and Brooksby et al. *Proc. Soc. Photo-Opt. Instr. Engin.* 2389: 564–570 (1995).

Acousto-optic imaging actually expands the ability of light imaging to provide functional imaging since the degree to which the focused sound waves interact with the light will depend upon the mechanical properties of the body at the focus site. The ability to measure tensile modulus and other mechanical properties of a suspicious lesion greatly facilitates identification of the lesion as malignant or benign.

Thus, in acousto-optic imaging the detected light signal carries a record of the interaction of ultrasound on the test object. Other phenomena also have this characteristic. In the phenomenon known as sonoluminescence, light is generated by the action of ultrasound on certain materials (see Suslick, "Ultrasound, its chemical, physical and biological effects", VCH, New York 1988). Modulation of the frequency or amplitude of the ultrasound may impart a modulation to the sonoluminescence, and detection at the modulation frequency provides a means of separating out from the background the signal due to the ultrasound irradiation.

The present invention is directed at improvements in light imaging procedures where the detected light signal is affected by ultrasound irradiation of the human or animal body under study and in particular to the use of contrast agents in such imaging procedures. These contrast agents are materials which scatter, emit or absorb (or do two or more of these) light in the 300 to 1300 nm wavelength range, preferably the 600 to 1300 nm wavelength range, whereby the detected light signal is affected or generated by the ultrasound irradiation of the body, by the presence in (or absence from) the ultrasound irradiated portion of the body of the contrast agent and optionally by the selective sensitivity of the contrast agent to differences in its microenvironment within the body.

Thus viewed from one aspect the invention provides a method of generating information from (e.g. an image of) an animate human or non-human (e.g. mammalian; avian or reptilian) animal body which method comprises:

administering to said body a physiologically tolerable material capable of absorbing, scattering or emitting light at a wavelength in the range 300 to 1300 nm;

subjecting at least a portion (or target zone) of said body to ultrasound irradiation;

detecting light in the wavelength range 300 to 1300 nm, preferably 600 to 1300 nm, from said portion of said body; and manipulating the detected light to generate said information (e.g. an image of at least part of said body).

By this method it is possible to to modify or enhance said information (e.g. to enhance contrast in an image of said portion or to facilitate determination of functional information regarding said portion, such as pH or oxygen content, etc.).

Viewed from an alternative aspect the invention provides a method of generating information from (e.g. an image of) an animate human or non-human (e.g. mammalian, avian or reptilian) animal body which method comprises:

administering to said body a physiologically tolerable material capable of modifying the generation or transformation of light within said body by ultrasound irradiation;

subjecting at least a portion of said body to said ultrasound irradiation;

detecting light from said portion of said body; and manipulating the detected light to generate said information (e.g. an image of at least part of said body).

The modifying effect of the said material is preferably an enhancing effect and the light detected and used for information generation preferably comprises ultrasound induced light.

The physiologically tolerable material (hereinafter referred to as the contrast agent) used in the methods of the invention may conveniently be one for which the contrast effect, e.g. the effect on light generation, light scattering, light absorption, light propagation or light frequency is dependent on microenvironment, e.g. pH, oxygen content, etc.

Viewed from a further aspect the invention provides the use of a physiologically tolerable material capable of absorbing, scattering or emitting light at a wavelength in the range 300 to 1300 nm, preferably 600 to 1300 nm for the manufacture of a composition for administration to the human or animal body in a method of diagnosis practised thereon which involves subjecting a portion of said body to ultrasound irradiation, detecting of light in the wavelength range 300 to 1300 nm, preferably 600 to 1300 nm from said portion and manipulation of the detected light to provide spatial and/or functional information (e.g. an image) relating to said portion.

Viewed from a still further aspect the invention provides the use of a physiologically tolerable material capable of modifying light generation or transformation within a human or animal body for the manufacture of a composition for administration to the human or animal body in a method of diagnosis practised thereon which involves subjecting a portion of said body to ultrasound irradiation, detecting of light from said portion and manipulation of the detected light to provide spatial and/or functional information (e.g. an image) relating to said portion.

In the methods of the invention, the ultrasound irradiation is preferably focused on a portion of the body to which the contrast agent distributes or at which the contrast agent has accumulated. The ultrasound irradiation moreover is preferably modulated, in frequency and/or amplitude, with a characteristic modulation pattern or frequency and the component of the detected light signal that is likewise modulated is preferably extracted and used to generate the desired information (e.g. image).

Where the contrast agent is not itself sonoluminescent, the method of the invention will generally involve exposing at least part of the ultrasound irradiated portion (the target zone) of the body with light having a wavelength in the range 300 to 1300 nm, preferably 600 to 1300 nm, preferably monochromatic, e.g. laser, light. Such irradiating light incident on the body may moreover be frequency and/or amplitude modulated. As one example of amplitude modulation, the incident light may be pulsed.

Where the body is thus illuminated, the detected light will generally correspond to a transmitted or scattered (e.g. reflected) component of the illuminating light or to light emitted by the contrast agent following absorption of the illuminating light (e.g. a fluorescence emission).

Where the body is illuminated, this may be with one or more, e.g. 1, 2, 3 or 4, non co-axial beams of light. Where a plurality of light beams are used, these may be at different wavelengths although generally it will be preferred to use beams of the same wavelengths. Moreover when a plurality of light beams are used these will generally be directed at the target zone and means will generally be provided for detecting light from each light beam that has passed through the target zone. Each beam may be amplitude- or frequency-modulated at the same frequency or at different frequencies. When the light is highly scattered in the body, the direction of illumination is arbitrary.

The contrast agent used for acousto-optic imaging according to the invention may take a variety of forms. Thus it may be a particulate (e.g. a solid or semi solid particle, a liquid droplet, a gas bubble, or a vesicle (e.g. a micelle, liposome or microballoon) with a rigid or flexible, continuous or porous membrane enclosing a gas, a gas-precursor (a material or mixture of materials which are gaseous at 37° C. or at temperatures generated by the ultrasound irradiation), a liquid, or a solid, or a mixture of two or more thereof.

For the sake of clarity, the word "particle" is used to refer to any physiologically acceptable particulate materials. Such particles may be solid (e.g. coated or uncoated crystalline materials) or fluid (e.g. liquid particles in an emulsion) or may be aggregates (e.g. fluid containing liposomes). Particulate material with a particle size smaller than or similar to the incident light wavelength is preferred.

Such particulates may be or include chromophores (materials or moieties which absorb and/or emit light at a wavelength in the range 300 to 1300 nm, preferably at a wavelength in the range 600 to 1300 nm) or may be essentially colourless (e.g. free from prominent absorption or emission maxima in the wavelength range 600 to 1300 nm). Thus for example particulate contrast agents may be materials which scatter light in the 300 to 1300 nm, preferably 600 to 1300 nm wavelength range by virtue of their size and difference in refractive index from that of surrounding body fluids in the target zone. Alternatively they may be composed of a light-absorbing dye with or without a colourless surrounding shell or membrane, or of a colourless core (solid, liquid or gaseous) surrounded by or coated with a light-absorbing dye. For sonoluminescence, particles with chromophores are particularly useful if they absorb light in a wavelength range outside the detection range. Where particulate, the contrast agent will preferably have a mean particle size in the range 5 nm to 20 µm (the upper end of the range generally being appropriate only for deformable particles), particularly 10 nm to 8 µm, especially 80 to 2000 nm and most preferably 100 to 500 nm.

Generally, lipophilic contrast agents will be formulated as oil-in-water emulsions with oil droplet sizes between 5 and 10000 nm, preferably between 10 and 2000 nm suspended in a pharmaceutically acceptable aqueous phase. Such oil droplets may be composed exclusively of radiation absorbing, scattering or fluorescing component(s) or may include other lipophilic substances distributed throughout the droplet. These emulsions will likely contain pharmaceutically acceptable excipients as are known in the art including lecithin, other phospholipids, surfactants such as the Tetronics and Pluronics, lipophilic additives such as sesame oil, and normally used components for isotonicity, pH and osmolality control.

The contrast agent may alternatively be a soluble material, e.g. a water-soluble chromophore or polychromophore, or a colourless soluble polymer which facilitates the generation of light by ultrasound.

Where the contrast agent is a, or contains at least one, chromophore, this is preferably a material or moiety which has an absorption maximum in the range 300 to 1300 nm, preferably 600 to 1300 nm, particularly preferably 650 to 900 nm.

For fluorophores, i.e. materials which absorb light and emit light at a different wavelength, the emission wavelength will preferably also be in the 600–1300 nm range. In this way the light the chromophore absorbs/emits is subject to minimal absorption by the body.

Where the contrast agent contains a chromophore, it may conveniently be one which has characteristic absorption/emission maxima which are sensitive to the microenvironment the contrast agent is in, e.g. pH, oxygen content etc. For particulate chromophore-free contrast agents, sensitivity to microenvironment may likewise be achieved by forming the particles from materials which change optical or mechanical properties (e.g. hardness, opacity, size etc.) according to the pH, oxygen content etc. of their microenvironment.

Thus the absorption wavelengths and acousto-optical properties of the contrast agent can be selected to be sensitive to the biochemical or biophysical properties of the organ or tissue to which they distribute enabling information concerning those biochemical or biophysical properties to be extracted from the light signals detected in the method of the invention.

The "information" generated in the method of the invention may be in the form of spatial, temporal and/or functional images, in the form of quantitated values for selected parameters for the target zone (e.g. pH, etc.), or simply in terms of an indication that a criterion is or is not met (e.g. pH is or is not different from that of surrounding tissue). Where quantitated values are generated, this will generally involve calibration against values for known standards.

Particulate or soluble contrast agents used according to the invention may if desired incorporate components serving to modify their biodistribution or bioelimination, e.g. targeting vectors (e.g. antibodies, antibody fragments, proteins, oligopeptides, receptor binding drugs, etc.) capable of causing the agent to accumulate at particular body sites, for example in tumors or at the surfaces of body ducts or cavities (e.g. in the gastrointestinal tract, lungs, vasculature etc.), or blood pool residence extenders (for example polyalkylene oxides, heparinoids and other materials which can delay abstraction from the blood stream of particulate or soluble materials). Examples of such vectors and blood pool residence extenders and their conjugation to particles and chromophores are given in our copending US Patent Application entitled "Method of Tumor Treatment" filed Apr. 29, 1997 and our copending International Patent Application No. PCT/GB98/01245 entitled "Method of Demarcating Tissue", which also list suitable chromophore and polychromophore materials.

In general, solid contrast agents will be formulated as particles with sizes between 5 and 10000 nm, preferably 10 and 6000 nm, suspended in aqueous solution. However, optimal light absorption and optimal light scattering will occur when the particles have diameters between 100 and 500 nm.

Optionally the solution in which solid particles are suspended may contain buffers and other excipients to control the pH and osmolality. Preferably the solid particles will be coated with a surfactant selected from, e.g. Pluronic F-68, Pluronic F-108, Tweens, Spans, and Tetronic T-908, to impede aggregation during autoclaving and storage.

In this invention, a surfactant molecule is defined as an emulsifier or detergent as listed in McCutcheon's Directories, Volume 1: Emulsifiers and Detergents (1994), and which contains at least one chemical functional group selected from the group consisting of an alcohol (OH), a nitrilo group including a primary amine ($NH_2$) and a secondary amine (NH), a carboxylic acid (COOH), a sulfhydryl (SH), a phosphoric acid group, phosphonic acid group, a phenolic group, a sulfonic acid group, a carbon-carbon double bond, and a ketone.

Chemical functional groups in the surfactant molecules can be interconverted by chemical reactions well known to those skilled in the art. For example, a hydroxyl group can be converted to a methanesulfonic acid ester which can be treated with sodium azide and reduced to form an amine group. Carboxylic acid groups and ketones can be reduced to form alcohols, and alcohols can be oxidized to form ketones, aldehydes, and carboxylic acid groups.

Useful surfactant molecules are emulsifiers or detergents which can function as dispersing agents, wetting agents, adsorbents, anticaking agents, soil antiredispositioning agents, antistats, binders, carriers, pearlescents, conditioning agents, hydrotropes, defoamers, emollients, flocculants, humectants, lubricants, opacifiers, plasticizers, preservatives, release agents, scale inhibitors, stabilizers, suspending agents, thickeners, UV absorbers, water repellants, waxes, and polishes, and which contain at least one chemical functional group selected from the group consisting of an alcohol (OH), a nitrilo group including a primary amine ($NH_2$) and a secondary amine (NH), a carboxylic acid (COOH), a sulfhydryl (SH), a phosphoric acid group, a phosphonic acid group, a phenolic group, a sulfonic acid group, a carbon-carbon double bond, and a ketone.

Preferably, the surfactant molecule comprises a polyalkyleneoxide moiety, optionally containing a branching group as defined herein; more preferably a polyalkyleneoxide block copolymeric moiety, optionally containing a branching group as defined herein; and most preferably a polyalkyleneoxide block copolymeric moiety optionally containing a branching group as defined herein and comprising a polypropylene oxide block and a polyethyleneoxide block. Examples of useful surfactant molecules include block copolymers such as AL 2070 available from ICI Surfactants, Antarox block copolymers available from Rhone-Poulenc, Delonic block copolymers available from DeForest, Inc., Hartopol block copolymers available from Texaco Chemical Canada, Macol block copolymers available from PPG Industries, Marlox block copolymers available from Huls America, Pluronic block copolymers including Pluronic F, L, P and R available from BASF Corp., Poly-Tergent block copolymers available from Olin Corp., and Tetronic and Tetronic R block copolymers available from BASF Corp. Currently preferred surfactant molecules include Tetronic and Pluronic block copolymers, and currently most preferred are Tetronic block copolymers.

When the agents are intended for injection into the vascular system, they may be coated with a substance such as poly(ethylene glycol) to slow clearance from the bloodstream.

Optionally, the surfactants and other compounds of this invention can be attached to a targeting vector so as to allow the particles to accumulate in certain locations of the body such as specific organs, parts of organs or diseased tissue. Methods for attachment are taught in WO 96/40285, its priority applications U.S. Ser. Nos. 08/497,684 and 08/640,464, and in 08/392,614.

Soluble dyes will be useful as contrast agents for acousto-optic imaging because they intensify the interaction between the light and the sound by increasing the difference in optical properties between the troughs and valleys of the acoustic wave. Such dyes will be especially useful if they are highly fluorescent. When the frequency of the ultrasound is properly chosen, it will modify the local environment around the dye and affect the fluorescence frequency. The ultrasound frequency should be between 0.01 and 10 MHz, especially 0.1 to 3 MHz, particularly 0.5 to 2.5 MHz. Modulation of the acoustic power at a frequency between 0 and 100 kHz, especially 0 and 30 kHz, particularly 0 and 10 kHz, will impart an amplitude modulation on the detected light at the same frequency. In addition, the detected light will be modulated at the frequency of the ultrasound. Detection of the light that is modulated at either frequency will facilitate separation of the signal carrying imaging or functional information from the background signal, which largely consists of scattered light from the impinging radiation.

Especially preferred as soluble dyes are polymeric substances with a molecular weight high enough to slow the clearance of the dyes from the blood stream. Such materials may consist of chromophores with attached polymer segments, or they may be substances in which the dyes are directly incorporated into the polymer backbone. Especially preferred for a linker between or for conjugation to dye chromophores are segments of poly(ethylene glycol). Examples of such dyes are disclosed in W097/13490 and in our copending US Patent Application entitled "Method of Tumor Treatment" filed Apr. 29, 1997 and our copending International Patent Application No. PCT/GB98/01245 entitled "Method of Demarcating Tissue" filed Apr. 29, 1998.

When soluble dyes are to be supplied as pre-made solutions, the solutions optionally may contain stabilizing agents as taught in WO 94/23646. The solutions may also contain excipients to control the pH or osmolality.

Soluble dyes may optionally be enclosed in vesicles (e.g. micelles or liposomes) as taught in WO 96/23424. Liposomal formulations may optionally contain substances to stabilize the dyes against oxidation or other degradative processes.

A preferred form of liposomal formulation contains dyes having in common with rhodamine 6G (Aiuchi, T.; Tanabe, H.; Kurihara, K.; Kobatake, Y., "Fluorescence Changes of Rhodamine 6G Associated with Chemotactic Responses in Tetrahymeena Pyriformis," Biochem. Biophys. Acta, 1980, 628, 355–364) and carboxyfluorescein (Chen, R. F.; Knutson, J. R., "Mechanism of Fluorescence Concentration Quenching of Carboxyfluorescein in Liposomes: Energy Transfer to Nonfluorescent Dimers," 1988, 172, 61–77) the property that they lose their fluorescence when encapsulated in liposomes. A standard method of preparation of liposomes of uniform size involves sonication. Under the influence of ultrasound the liposomes break and reform. In the body the effect of the focused ultrasound will be to release dye selectively at the focusing site. The detection of fluorescence from that site then pinpoints its location.

Liposomes that release fluorescent dye will be particularly useful as contrast agents when the amplitude of the ultrasound has a frequency between 0.01 and 10 MHz, especially 0.1 to 3 MHz, particularly 0.5 to 2.5 MHz, and is modulated at a characteristic frequency between 0 and 100 kHz, especially 0 to 30 kHz, particularly 0 to 10 kHz. Then the component of the detected signal that directly reflects the location and properties of the site of sound focusing will be also modulated at that frequency and can easily be separated from background. The most effective modulation frequency will be chosen to reflect the rate at which dye is released and recaptured from the liposomes.

Contrast agents for acousto-optic imaging may also have the form of gas-filled bubbles in which dyes having in common with rhodamine 6G and carboxyfluorescein the property that they lose their fluorescence when encapsulated in liposomes are incorporated into the shells. Except for the presence of the dye, these bubbles will have a form similar to that of contrast agents for ultrasound imaging. Heating of the gas contained within these bubbles by ultrasound will lead to expansion of the gas, rupture of the bubbles, and release of the fluorescent dyes. Again, these agents may contain agents on the surface such as PEG to slow blood clearance or may have attached specific targeting vectors.

Sonoluminescence is associated experimentally with the collapse of microbubbles produced by high-intensity ultrasound (cavitation) (Suslick, K. S., ed., "Ultrasound, Its Chemical, Physical, and Biological Effects," VCH, New York, 1988). Bubble formation is facilitated by solid particles acting as nucleation centers. Contrast agents consisting of suspended particles with diameters between 200 and 5000 nm will be particularly useful as contrast agents for sonoluminescence. These should be as large as possible within the biological constraints necessary to prevent adverse reactions. In general, the suspended particles will have substances such as poly(ethylene glycol) on their surfaces to slow uptake by macrophages within the body and to prolong blood lifetime. Optionally they may contain specific targeting vectors. Optionally they may also have attached materials to scavenge free radicals that are produced by the cavitation process.

Alternatively contrast agents without radical scavengers will be useful for monitoring therapeutic procedures in which targeted ultrasound is used to destroy diseased lesions.

Cavitation is known to result in the formation of free radicals. When these radicals interact with precursors to form colored free radicals, they can be used for the generation of markers of the site of ultrasound focusing that can detected by optical imaging and used as an indication of where the ultrasound is concentrated. This method will be especially useful when the ultrasound is used for therapeutic purposes, for example, the selective destruction of cancerous lesions, as well as for imaging.

Water soluble polymers will facilitate the generation of light by ultrasound. The water soluble polymers used according to the invention conveniently have a molecular weight (MW) of 150 to 1000000 (especially 500 to 500000, most preferably 1 to 50000), and preferably are hexamers or higher polymers. The polymers preferably contain monomer residues contributing 2 to 6 atoms to the polymer backbone, especially 2, 3 or 4 atoms. The polymers may conveniently comprise residues of monomers such as alkylene oxides, hydroxyalkyl-acrylates or methacrylates, vinyl alcohol, vinyl pyrrolidone, acrylamide, styrenes, etc. Especially preferably, the polymers will be polymeric surfactants.

Examples of suitable polymers include: polyalkylene oxide polymers and copolymers (including random and block and graft copolymers) and oligomers such as poly(ethylene oxide) also known as poly(ethylene glycol) also known as PEG, as well as poloxamers and poloxamines (also known as Pluronics and Tetronics); PEG derivatives such as PEG mono- and bis-ethers of alkyl, alkenyl and alkynyl groups containing from 1 to about 26 carbon atoms and which can be linear or branched and which can comprise a cycloalkyl or cycloalkenyl group with ring size of from 3 to 10 carbons (preferably a cyclohexenyl, cyclooctenyl, or cyclooctadienyl group) such that this total number of carbons in the group is less than 26; PEG mono- and bis-esters (including alpha-methoxy-PEG monoesters) and PEG mono- and bis-amides (including alpha-methoxy-PEG monoamides) of alkyl, alkenyl and alkynyl carboxylic acid groups containing from 1 to about 26 carbon atoms and which can be linear or branched and which can comprise a cycloalkyl or cycloalkenyl group with ring size of from 3 to 10 carbons (preferably a cyclohexenyl, cyclooctenyl or cyclooctadienyl group) such that the total number of carbons in the group is less than 26; and derivatives of PEG as described above conjugated to a polyiodinated aromatic compound, e.g. PEG esters and amides of mono, di, and tri-iodinated aromatic benzoic acid derivatives such as diatrizoic acid esters and amides; poly(propylene glycol) (PPG, also known as poly(propylene oxide)) and PPG derivatives and PEG-PPG random and preferably block copolymers, poly(hydroxyalkyl) acrylates and methacrylates, polyvinyl alcohol, polyvinylpyrrolidone, polyacrylamide, water soluble polystyrenes including sulfonated polystyrene, hydroxyalkylated and polyhydroxyalkylated polystyrene, and PEG esters and esters of hydroxyalkylated and polyhydroxyalkylated polystyrene; surfactants comprising PEG and hydroperoxides and peroxides of PEG, such as pluronics (e.g. Pluronic-F108 from BASF).

When the polymer comprises a polyalkylene oxide, the polyalkylene oxide moiety can be linear or branched and is preferably a homopolymeric or copolymeric, especially block copolymeric, moiety containing repeat units $C_nH_{2n}O$ where n is 2,3 or 4, preferably 2 or 3, especially preferably $CH_2CH_2O$, $OCHCH_3CH_2$, $CH_3CHCH_2O$ or $CH_2CH_2CH_2O$ repeat units. Within the PAO moiety, one or more, preferably one or two, of the ether oxygens may be replaced by an amine group NH or NE where E is a bond or an alkyl or hydroxyalkyl group or a $(C_nH_{2n}O)_qE'$ side chain (where n is 2,3 or 4 and q is an integer, the maximum value for which is set by the molecular weight limit for the PAO and E' is H or alkyl, a chemical bond or a chromophore).

Any alkyl, alkenyl or alkynyl moieties, unless otherwise defined, preferably have up to 12, especially preferably up to 6 carbons.

In one aspect, a branching group in the backbone of the polyalkylene oxide moiety can be selected from the group consisting of a nitrogen atom and a carbon atom. At least one additional polyalkylene oxidyl group can be attached to the branching group by a chemical bond selected from the group consisting of carbon-carbon, carbon-nitrogen, and carbon-oxygen chemical bonds, or by a linking group.

Preferred linking groups to a nitrogen branching group include:

methylene groups, [—$CH_2$—];

poly(methylene) groups, [—$(CH_2)_n$—] wherein n is an integer from 2 to about 16, such as can be formed by reaction between a nitrogen NH group and an alkylenyl group containing a terminal halide (e.g., Cl, Br, I) or sulfonate group (e.g., methanesulfonate, toluenesulfonate, benzenesulfonate and the like);

alkylenecarbonyl groups [—$(CH_2)_{n"}$—$C(=O)$—] wherein n" is an integer from 1 to about 16 such as can be formed by reacting an NH group with a haloalkylenecarbonyl group;

ethylenesulfonylethylene groups [—$CH_2CH_2$—$S(=O)_2$—$CH_2CH_2$—], such as can be formed by reacting an NH group with a vinylsulfonylethylene group [$CH_2=CH$—$S(=O)_2$—$CH_2CH_2$—];

ethylenesulfonylmethyleneoxymethylenesulfonylethylene groups [—$CH_2CH_2$—$S(=O)_2$—$CH_2$—$O$—$CH_2$—$S(=O)_2$—$CH_2CH_2$—], such as can be formed by reacting an NH group with a vinylsulfonylmethyleneoxymethylenesulfonylethylene group [$CH_2=CH$—$S(=O)_2$—$CH_2$—$O$—$CH_2$—$S(=O)_2$—$CH_2CH_2$—];

ethylenesulfonylmethylenesulfonylethylene groups [—$CH_2CH_2$—$S(=O)_2$—$CH_2$—$S(=O)_2$—$CH_2CH_2$—], such as can be formed by reacting an NH branching group with a vinylsulfonylmethylenesulfonylethylene group [$CH_2=CH$—$S(=O)_2$—$CH_2$—$S(=O)_2$—$CH_2CH_2$—];

carbonyl groups [—$(C=O)$—] which can comprise an amide linking group formed, for example, by reacting an NH branching group with an activated ester such an N-hydroxysuccinimidyl-ester, or with a mixed anhydride such as a trifluoromethyloxycarbonyl-, or with an acid halide such as an acid chloride, e.g., Cl—$(C=O)$—;

sulfonyl groups [—$S(=O)_2$—] which can comprise a sulfonamide linking group formed, for example, by reacting an NH branching group with a sulfonyl halide such as a polyalkylene oxidylalkylenesulfonyl chloride, e.g., Cl—$S(=O)_2$—$(CH_2)_n$—O—PAO; wherein n is an integer from 2 to about 16 and PAO is a polyalkylene oxidyl group;

carbonyloxy groups [—$C(=O)$—O—] such as those found in urethane groups such as can be obtained by reacting a polyalkyleneoxy group with phosgene and then with an NH group;

thiocarbonyl groups [—$(C=S)$—] such as those found in thiourethane groups such as can be obtained by reacting a polyalkyleneoxy group with thiophosgene and then with an NH group;

alkylenecarbonyloxymethyleneoxycarbonylalkylene groups [—(—CH$_2$—)$_{n'}$—C(=O)—O—C(R'R")—O—C(=O)—(—CH$_2$—)$_{n'}$] where each n' is independently selected from the group of integers from 1 to 16 and each R' and R" is independently selected from the group consisting of H and methyl; and, carbonylalkylenecarbonyl groups [—C(=O)—(CH$_2$)$_w$—C(=O)—] wherein w is an integer from 1 to about 6, such as succinate and adipate.

Preferred linking groups to a carbon branching group include:

ether groups [—O—];

thioether groups [—S—];

thiosulfoxide groups [—S(=O)—];

thiosulfonyl groups [—S(=O)$_2$—];

oxycarbonyl groups [—O—C(=O)—];

aminocarbonyl groups [—NH—C(=O)—];

carbonyl groups [—(C=O)—];

carbonyloxy groups [—C(=O)—O—];

carbonate groups [—O—C(=O)—O—];

carbonyloxymethyleneoxycarbonylalkylene groups [—(—C(=O)—O—C(R'R")—O—C(=O)—(—CH$_2$—)$_{n'}$—] where n' is an integer from 1 to 16 and each R' and R" is independently selected from the group consisting of H and methyl;

urethane groups [—O—C(=O)—NH—]; and thiourethane groups [—O—(C=S)—NH—].

In another aspect, a branching group can comprise the unit —NR$_{1'}$—CR$_{2'}$R$_{3'}$—CR$_{4'}$R$_{5'}$— wherein R$_{1'}$ can be selected from the group consisting of H, an alkyl group of from 1 to about 16 carbon atoms which may be linear, branched, saturated, unsaturated, or contain a carbocyclic ring of from 3 to about 10 carbon atoms, or a carbonylalkyl group wherein the alkyl group is defined immediately above;

R$_{2'}$ and R$_{3'}$ are independently selected from the group consisting of H, an alkylene group of from 1 to about 16 carbon atoms, which may be linear, branched, saturated or unsaturated, and can contain a carbocyclic ring of from 3 to about 10 carbon atoms and to which is attached a polyalkylene oxidyl group through a heteroatom group selected from the group consisting of NH, O, S, O—C(=O), and C(=O)—O, e.g., such as 4-(polyalkyleneoxyethylcarbonylaminobutyl), [PAO—CH$_2$CH$_2$C(=O)NH—(CH$_2$)$_4$—, 2-(polyalkyleneoxycarbonyl)ethyl, [PAO—C(=O)CH$_2$CH$_2$—], polyalkyleneoxycarbonylmethyl, [PAO—C(=O)CH$_2$—], polyalkyleneoxyethylaminocarbonylmethyl, [PAO—CH$_2$CH$_2$NHC(=O)CH$_2$—], polyalkyleneoxyethylaminocarbonylethyl, [PAO—CH$_2$CH$_2$NHC(=O)CH$_2$CH$_2$—], polyalkyleneoxymethyl, [C], and polyalkyleneoxyethylthiomethyl, [PAO—CH$_2$CH$_2$—S—CH$_2$—];

R$_{4'}$ and R$_{5'}$ are independently selected from the group consisting of H, an alkyl group of from 1 to about 16 carbon atoms which may be linear, branched, saturated, unsaturated, or contain a carbocyclic ring of from 3 to about 10 carbon atoms, or a carbonylalkyl group wherein the alkyl group is defined above, or, preferably, where both R$_{4'}$ and R$_{5'}$ are taken together form a carbonyl group;

and wherein at least one of R$_{2'}$R$_{3'}$ is not H.

Preferred units —NR$_{1'}$—CR$_{2'}$R$_{3'}$—CR$_{4'}$R$_{5'}$— are selected from the group consisting of lysine, aspartic acid, glutamic acid, cysteine, and serine in the backbone of the polyalkylene oxide moiety and contain least one additional polyalkylene oxide attached, for example, to the epsilon amine site of lysine, to the gamma carboxylic acid site of aspartic acid, to the delta carboxylic acid site of glutamic acid, to the beta sulfhydryl group in cysteine, and to the beta hydroxy site of serine.

In another aspect, one branching group and a carbon atom in the backbone of the polyalkylene oxide moiety or two branching groups in the backbone of the polyalkylene oxide moiety can be joined by an alkylene group of from 2 to 12 carbon atoms. The alkylene group can be linear or branched such as ethylene, propylene, butylene, isobutylene, pentylene, hexylene, octylene, decylene, and dodecylene. The alkylene group can be saturated or unsaturated such as 2-butenylidene, isoprenylene, and 2-butynylidene. In another aspect, the alkylene group can comprise a saturated or unsaturated cyclic group such as cyclopropylidene, cyclobutylidene, 1,2-cyclopentylidene, 1,3-cyclopentylidene, 1,2-cyclohexylidene, 1,3-cyclohexylidene, 1,4-cyclohexylidene, a cyclohexenylidene ring such as can be formed by a Diels-Alder reaction between a diene and a dieneophile, 1,4-cycloheylidenebismethylene, ethylene-1,2-cyclopropylidenemethylene, 1,1-spirocycloproylidenebismethylene, and the like, and which can contain an oxygen or sulfur ether atom, such as a 2,5-tetrahydrofuranylene group and a 2,6-tetrahydro-pyranylene group.

In another aspect, one branching group and a carbon atom in the backbone of the polyalkylene oxide moiety or two branching groups in the backbone of the polyalkylene oxide moiety can be separated by an aromatic ring of 6 to 14 carbon atoms such as p-phenylene, or m-phenylene, or m-toluidene, 9,10-anthracenylidene, or 1,4-naphthalenylidene, or an aralkylene group such as p-phenylenebismethylene, or 9,10-anthracenylidenebismethylene, and which aromatic ring can comprise a 5- or 6-membered heterocyclylene group containing one or two heteroatoms selected from the group consisting of nitrogen, oxygen, and sulfur such a 2,6-pyridinylene, 1,4-imidazolidene, 5,8-quinolinylidene, and 1,1-spiro-2,6-dithiacyclohexylene, or a symmetrical triazinylene group.

The polymeric compounds may be homo- or copolymers, and where copolymers may be random, block or graft, and may contain individual comonomer residues such as the diamine residues in the poloxamine polymers. Poly(alkylene oxide) polymers are especially preferred.

Such poly(alkylene oxide) compounds are readily available commercially, e.g. as Pluronics, Tetronics or PEGs of various molecular weights.

The poly(alkylene oxides) may contain a poly(alkylene oxidyl) moiety (e.g. a moiety of formula ((X)$_n$O)$_p$, where X is an alkylene group (e.g. a C$_{2-4}$ alkylene) and n and p are positive integers (n conveniently being 1 to 5 and p from 1 to 20000), optionally incorporating an alkylene-amino or alkylenediamino group such as an ethyleneamine or ethyienediamine group) and may consist simply of such a moiety terminated by simple functional groups, e.g. hydroxyl, amine, sulphate carboxylate, phosphate and phosphonate groups.

Conjugates of the polymers used according to the invention may contain moieties, other than the water soluble (i.e. hydrophilic) polymer moiety, covalently bonded together, e.g. chromophores, lipophilic groups (e.g. phospholipid groups), biotargetting vector groups, and groups detectable in in vivo diagnostic imaging modalities such as for example MR and X-ray (e.g. CT) imaging.

Preformed encapsulated gas bubbles are especially preferred as contrast agents for sonoluminescence imaging. Similar gas-filled bubbles are useful as contrast agents for ultrasound imaging. The enclosed gas may be air, xenon, argon, helium or any other physiologically acceptable gas. Mixtures of gases such as xenon and nitrogen, argon and nitrogen, and helium and nitrogen are also within the scope of the invention. A preferable mixture is 1 to 99% xenon in nitrogen. Especially preferable is a mixture of 1 to 10% xenon in nitrogen.

Particular examples of materials suitable for use as contrast agents for sonoluminescence imaging in the present invention are: particulate suspensions containing 1,1',3,3,3',3'-hexamethylindotricarbocyanine iodide, prepared as described in Example 1 of WO 97/13490; and the compounds of Examples 1–7 of WO 96/17628; all of which Examples are incorporated herein by reference.

In the methods of the invention, the contrast agent is administered to the subject (e.g. a human patient) under investigation in a manner such that it may reach the target zone of interest, e.g. the breast, brain, liver, lymph nodes, skin lesion etc. Such administration may be by any conventional route, e.g. administration into the gastrointestinal tract, injection or infusion into the vasculature, subcutaneous, intramuscular or interstitial injection or infusion, sublingual or nasal administration, administration into the lungs, vagina, bladder or uterus, topical or transdermal application, etc. In general, injection or infusion into the vasculature, subcutaneous or interstitial administration, topical application or administration into the gastrointestinal tract will be preferred. Administration may take place at the target zone or at a site from which the contrast agent is transported to the target site, e.g. by uptake through the walls of the gastrointestinal tract or by transport within the blood vessels. Information recording (e.g. image generation) may take place before the contrast agent has reached the target zone but in that event will also take place after the contrast agent has reached the target site.

For the information generation procedure, the target zone is irradiated with ultrasound, preferably focused ultrasound, e.g. of frequency 0.01 to 10 MHz, especially 0.1 to 3 MHz, particularly 0.5 to 2.5 MHz. The ultrasound irradiation may be continuous and uniform at the target zone or more preferably may be frequency- and/or amplitude-modulated. One form of amplitude modulation that may be used is pulsed ultrasound. In general however frequency and amplitude modulation will involve imposition of a variation in frequency and/or amplitude which has its own characteristic frequency (the ultrasound modulation frequency). The modulation frequency will be between 0 and 100 kHz, especially 0 and 30 kHz, particularly 0 and 10 kHz.

Where the contrast agent is sonoluminescent and the information is generated using detected sonoluminescent emissions, the ultrasound is preferably modulated, especially amplitude-modulated. Particularly preferably the amplitude minima are below the level where resulting sonoluminescence is detectable while the amplitude maxima are above that level. In this case the generated light will be modulated at the modulation frequency and harmonics thereof. Detection of the amplitude of the light at one or more of those frequencies will facilitate separation from the background of light from ambient sources. Where spatial resolution is not critical, and where background noise is reduced or eliminated (e.g. by conducting the procedure in the dark or in visible light filtered to remove red to near infra-red components) it may not be necessary to extract a modulated component from the detected light signal.

Where the frequency of the sonoluminescent emission is dependent on the microenvironment of the contrast agent, the detected light may be filtered or frequency analysed to separate out the components generated under different conditions, e.g. of pH or oxygen concentration, and so provide information about the physicochemical nature of the target zone.

Where the detected light is sonoluminescence, it is especially preferred that the ultrasound irradiation be focused to ensure that the detected signal derives from a clearly locatable target zone. For this reason, the use of the quasi-ballistic component of the sonoluminescence (i.e. that component which follows a relatively straight path from the light generation site to the first part of the light detector assembly it meets) may also be preferred.

Where sonoluminescence generation is dependent on the frequency of the ultrasound irradiation, modulation of the ultrasound frequency may be used in the same way as modulation of ultrasound amplitude to select a relatively low noise component of the detected light signal from which to generate the desired information or image.

In embodiments of the invention where the contrast agent is not sonoluminescent, the target zone will also be illuminated with light of a frequency in the range 300 to 1300 nm, preferably 600 to 1300 nm especially 650 to 900 nm. Such light may be polychromatic and polydirectional; however, preferably one will use a substantially monochromatic focused light beam, especially preferably a laser beam, e.g. from a tunable dye laser. The incident light may again be modulated in amplitude and/or frequency, with amplitude modulation being preferred. As with the ultrasound modulation discussed above, modulation of the incident light beam at a characteristic modulation frequency and analysis of the detected light signal and extraction of a component also modulated at that characteristic modulation frequency allows generation of information and images using a signal containing lower level of noise.

Where the interaction of contrast agent and illuminating light is a scattering interaction, e.g. where the contrast agent is a chromophore-free particulate, the detected light signal may be frequency analysed to extract the component which is Doppler shifted by interaction with ultrasound in the target zone, thereby again reducing the noise level in the component used for information generation. Similarly, if desired, the quasi-ballistic component of the detected amplitude (or frequency) modulated incident light may be used for information generation.

Where in the methods of the invention the contrast agent emits light or scatters light, it is particularly preferred to detect the quasi-ballistic component of the light from the target zone. Where the target zone is illuminated, the presence of a contrast agent may reduce the quasi-ballistic component of the transmitted irradiating light, i.e. the quasi-ballistic component along the optical axis between light source and light detector. However, away from that axis the quasi-ballistic component of light originating from or scattered in the target zone will be increased.

In the method of the invention, ultrasound irradiation is preferably effected using a focused transducer, e.g. a 3.5 MHz transducer with a focal length of 12.5 cm operating with a driving electrical signal at 3.5 MHz consisting of 50 $\mu$sec pulses with peak voltages of 100 volts and a repetition rate of 40 Hz. Generally, the ultrasound frequency can be between 0.1 and 10 MHz and the focal length should be between 1 and 20 cm. The peak pressure at the focus should be less than 50 bars. Any laser illumination is preferably at a power level of 10 milliwatts or less. Light detection may be effected using conventional photodetectors, preferably a photomultiplier tube such as the Hamamatsu HC. 123-01. To minimise "noise", the detections may be shielded to prevent light other than from the subject under study from reaching the photodetectors.

Ultrasound irradiation and light irradiation and detection may be effected using devices located externally of the subject under study or alternatively using devices inserted into a body cavity through a natural or surgically produced orifice.

All of the publications referred to herein are incorporated herein by reference.

The contrast agents of the invention may be administered to patients for imaging in amounts sufficient to be effective in the particular technique.

The dosage of the contrast agents will depend on the site being investigated, the nature of the contrast agent and the details of the imaging procedure. For intravenous feeding with emulsions, doses up to 1000 mg/kg/day have generally proven safe, but for imaging the doses will generally be 0.1 to 10 ml/kg of the suspension or 15 to 1500 mg/kg of the oil component of the suspension. For suspended solids the dose will vary from 100 to 500 mg/kg of the solid. For polymers the dose will vary from 1 to 700 mg/kg.

The contrast agents may be formulated with conventional pharmaceutical or veterinary aids, for example emulsifiers, fatty acid esters, gelling agents, stabilizers, antioxidants, osmolality adjusting agents, buffers, pH adjusting agents, etc., and may be in a form suitable for parenteral or enteral administration, for example injection or infusion or administration directly into a body cavity having an external escape duct, for example the gastrointestinal tract, the bladder or the uterus. Thus the contrast agents may be presented in conventional pharmaceutical administration forms such as tablets, capsules, powders, solutions, suspensions, dispersions, syrups, suppositories etc. However, solutions, suspensions and dispersions in physiologically acceptable carrier media, for example water for injections, will generally be preferred.

The contrast agents may therefore be formulated for administration using physiologically acceptable carriers or excipients in a manner fully within the skill of the art. For example, the contrast agents, optionally with the addition of pharmaceutically acceptable excipients, may be suspended or dissolved in an aqueous medium, with the resulting solution or suspension then being sterilized.

For some portions of the body, the most preferred mode for administering the contrast agents is parenteral, e.g. intravenous administration. Parenterally administrable forms, e.g. intravenous solutions or dispersions, should be sterile and free from physiologically unacceptable agents, and should have low osmolality to minimize irritation or other adverse effects upon administration, and thus the contrast medium should preferably be isotonic or slightly hypertonic. Suitable vehicles include aqueous vehicles customarily used for administering parenteral solutions or dispersions such as Sodium Chloride Injection, Ringer's Injection, Dextrose Injection, Dextrose and Sodium Chloride Injection, Lactated Ringer's Injection and other solutions such as are described in Remington's Pharmaceutical Sciences, 15th ed., Easton: Mack Publishing Co., pp. 1405–1412 and 1461–1487 (1975) and The National Formulary XIV, 14th ed. Washington: American Pharmaceutical Association (1975). The solutions or dispersions can contain preservatives, antimicrobial agents, buffers and antioxidants conventionally used for parenteral solutions, excipients and other additives which are compatible with the dyes and which will not interfere with manufacture, storage or use.

The invention will now be described further with reference to the following non-limiting Examples.

EXAMPLE 1

Optionally Photolabelled Nanoparticulate Suspensions (Prepared as Described in WO 96/23524)

A solution of WIN 70177 (an iodinated contrast agent prepared as described in WO 96/23524 and, optionally fluorescein in the molar ratio 100:1, optimally 50:1, most optimally 25:1, in DMSO (or DMF) is precipitated in water. The resulting precipitate is milled as described in U.S. Pat. No. 5,145,684 together with a surfactant stabilizer (e.g. Pluronic-F108 or Tetronic T-908 or 1508) to a particle size of 0.2 $\mu$m and dispersed in a medium to a contrast agent concentration of 0.5 to 25% by weight and a surfactant concentration of 0.1 to 30% by weight. A cloud point modifier such as poly(ethylene glycol) 400 (PEG 400) or propylene glycol as disclosed in U.S. Pat. No. 5,352,459 may also be included to ensure stability on autoclave stabilization.

EXAMPLE 2

Suspended Dye Particulates

The poorly soluble dye 3,3'-diethylthiatricarbocyanine iodide (Fisher) is added to a 1.5 oz brown glass bottle containing approximately 12 ml of 1.1 mm diameter beads of zirconium sulfate in an amount sufficient to be 15% (wt/vol) of the final suspension. The solution in the bottle is also made 3% in Pluronic F-68 and 10% in PEG-400 (Shearwater). It is milled at approximately 150 rpm for up to a total of 9 days, during which time the particle size is monitored by light scattering or other analytical methods. The process is stopped when the average particle size is 100–400 nm. The resulting product will have an absorption maximum around a wavelength of 772 nm and may be autoclaved without change in particle size.

EXAMPLE 3

Photolabelled Liposomes

A liposome suspension is prepared using a 0.01 M solution of rhodamine 6G and 5 to 10% of a phospholipid (10:1 ratio of lecithin to dipalmitolylphosphatidyl serine). Preparation is effected by conventional techniques (e.g. ultrasonication), followed by extrusion through controlled pore size filters and diafiltration or microfluidization. The resulting liposomes are steam sterilizable and are sterile filterable.

EXAMPLE 4

Preparation of Nanoparticle suspension of WIN 72115

Nanoparticle WIN 72115 (a fluorescent iodinated contrast agent) was prepared by combining WIN 72115 (prepared as described in Example 21 of WO 96/23524) and Pluronic F108 (BASF, Parsippany, N.J.) in a glass jar at concentrations of 15 gm/100 ml suspension and 3 gm/100 ml suspension. The jar was then half filled with 1.0 mm diameter zirconium silicate beads and sufficient water added to complete the required concentrations of agent/surfactant as noted above. Alternatively, the surfactant can be dissolved in the water before addition to the jar (with or without sterile filtration through 0.2 micron filters).

The jar is then rolled on its side for not less than 24 hours or more than 14 days at a rate of rotation sufficient to cause the beads within the jar to "cascade" down the walls of the jar as it turns (see U.S. Pat. No. 5,145,684). At the end of the milling cycle, the material is harvested from the jar and separated from the milling beads.

Nanoparticles of WIN 72115 prepared in this manner have an average particle size of 225 nm by light scattering.

WIN 72115 was designed to be excited with incident radiation from an Argon Ion laser. (in the green, near 514 nm) and emit light at wavelengths above that value. Thus, after injection, illumination of the patient with green light would stimulate emission of light of a slightly different wavelength that could be used for diagnostic purposes. Ultrasound irradiation will shift and modulate the frequency of the observed signal. The key features of this agent are that it can be prepared as nanoparticles, remain within the vasculature for greater than 15 minutes, provide both scattering and fluorescence contrast for light imaging.

In place of WIN 72115, the photolabelled agent of Example 22 of WO 96/23524 may be used.

EXAMPLE 5

Preparation of WIN 70146 in Pluronic F108 (I-404)

WIN 70146 (prepared as in Example 23 of WO 96/23524) was milled with 1.1 mm diameter zirconium silicate beads for 3 days under aseptic conditions. The concentration of this agent was 15% WIN 70146 in the presence of 4% Pluronic F-108. No additional salts or surfactants were added. The average particle size of the resulting nanoparticle suspension was 162 nm as determined by light scattering.

EXAMPLE 6

Preparation of an Autoclavable Formulation of WIN 70146 Using Pluronic P-108 and PEG 400

WIN 70146 (prepared as in Example 23 of WO 96/23524) was milled with 1.1 mm diameter zirconium silicate beads in the presence of Pluronic F-108 for 3 days. The final particle size was determined to be 235 nm. At this point, sterile PEG 400 was added to the suspension such that at completion, the formulation contained 15% (wt/vol %) WIN 70146, 3% (wt/vol %) Pluronic F-108 and 10% PEG 400. This formulation was then autoclaved under standard conditions (ie. 121 degrees C for 20 min.) resulting in a final particle size of 248 nm.

EXAMPLE 7

Preparation and Acute Safety Testing of Nanoparticle Suspensions of WIN 70146 in Pluronic F108

Particulate WIN 70146 was prepared as in Examples 23 and 10 of WO 96/23524 and injected into the tail vein of mice at doses of 3 ml/kg, 15 ml/kg, and 30 ml/kg (i.e. 0.45 gm/kg, 2.25 gm/kg and 4.5 gm/kg). No untoward effects were noted in any of the mice at any dose for a period of 7 days after which time the animals were sacrificed. Gross observation of these animals did not reveal any obvious lesions or disfigurations.

Further in-depth safety studies in rats have not revealed significant safety issues due to a single dose of WIN 70146/F108 at levels up to and including 30 ml/kg (4.5 gm/kg). These studies included in-depth histopathology, clinical chemistry, and in life observations.

EXAMPLE 8

Formulation of Indocyanine Green in a Liposome

Indocyanine Green (ICG) was added to a liposome suspension formed from 8.2% lecithin (phosphatidyl chloline), 0.8% dimyristalphosphatidylglycerol, and 0.1% of a nonionic, polymeric surfactant, P-79 which is designed to impart prolonged blood pool residence to the liposome. The phospholipids and the surfactant were mixed in water using ultrasonic energy from a probe sonicator (Bransonic Sonifer 450, 90% duty cycle, output 10). Liposomes were prepared using a Microfluidics M110S microfluidizer at 14,000 PSI and 4 passes through the interaction chamber of the phospholipid mixture. The resulting liposomes were approximately 100 nm in average diameter as determined by light scattering and remained the same size after autoclave sterilization. In addition, the liposomes were able to pass through a sterile filter (i.e. 0.2 micron pore size). Addition of ICG in sufficient amount to make the suspension approximately 7 mg/ml in ICG did not alter the physical characteristics of the liposomal suspensions. After sterilization under a nitrogen atmosphere, these ICG liposomes were stable for at least 6 weeks at room temperature.

Assessment of the spectral properties of the liposomal ICG relative to OCG dissolved in water or saline solution demonstrated the impact of the liposomal environment. Both the excitation maximum wavelength and emission maximum wavelength were shifted to lower energies (i.e. higher wavelengths) relative to the homogeneous water solutions.. In addition, careful measurements of quantum yield demonstrated at least a 4-fold increase in quantum yield of the liposomal ICG relative to the aqueous ICG solutions.

It is expected that radiation with light of the absorbence maximum of ICG together with simultaneous ultrasound irradiation will afford a significant advantage in detection of the fluorescent emission from the ICG. The advantage with respect to fluorescence will derive from the possibility that enhanced quantum yield of ICG within the liposome may be modulated by the ultrasound source affording better detection or phase-sensitive detection.

Light imaging detection of the fluorescence of ICG can be further enhanced by using a difference technique wherein the image without ultrasound is subtracted from that with the ultrasound, especially if the ultrasound is tuned such that the liposomes are ruptured thereby altering the fluorescent signal of the ICG within. This will afford enhanced sensitivity especially if the ultrasound or the input light signal or both are modulated to further differentiate the light signal from non-modulated background tissue signals. The recommended dose of the liposomal suspension of ICG for the imaging is 0.1 to 15 ml/kg.

EXAMPLE 9

Liposomal Suspension of X-ray Absorbing Dye for Acousto-optic Imaging

Liposomes (CTP-10) of phosphotidyl choline and phosphatidyl serine in a molar ratio of 10 to 1 were prepared by extrusion through stacked 1 micron pore size filters under pressure. These liposomes were prepared in a solution which contained 400 mg/ml iodixanol, an iodinated, soluble X-ray contrast agent. Thus, each liposome contained a significant amount of iodinated contrast agent within the internal aqueous pool of the liposome. This formulation of liposome encapsulated CT X-ray contrast agent (i.e. iodixanol) was administered to rabbits as a single bolus of 150 mg iodine/kg, a divided bolus of 2×75 mg iodine/kg, and a 10 minute infusion of 80 mg I/minute (total dose=800 mg I or approximately 265 mg iodine/kg at 1 ml/min). X-ray imaging was carried out on a GE spiral CT scanner at Palo Alto Veterans Hospital, Palo Alto, Calif. Neither the single bolus nor the divided bolus afforded significant blood opacification beyond 1 minute post administration. The infusion, however, provides useful opacification of the blood during the infusion as well as liver enhancement. Even at 5 minutes into the infusion, the contrast in the aorta is approximately 125 HU, at least 50 HU above background opacification levels.

With respect to acousto-optic imaging the CT data clearly show the levels of contrast agent present within the various structures (i.e., liver, blood). The current wisdom in the field is that every 30 HU is approximately 1 mg/g of iodine or more approximately 2 mg contrast agent/g of tissue. Thus, contrast agent levels up to 8 to 10 mg/g tissue are achieved in the above dosing regimens. These liposomes are known to be very good scattering agents over a wide rage of light wavelengths. Thus, under the influence of a modulated ultrasound source, transmitted light could be similarly modulated and afford a sensitivity advantage over traditional ballistic or semi-ballistic light for imaging the body. If the incident light beam could be modulated either electronically or via a shutter at the same frequency as the ultrasound or a harmonic frequency, the acousto-optic signal (from scattering) would be modulated also such that the background interference would be reduced.

For sonoluminescence imaging, the particles will serve as nucleation sites for bubble formation. The growth and collapse of these bubbles is required for light generation.

EXAMPLE 10

Preparation of a Stable Emulsion of Sudan III

Sudan III (also known as D&C Red No. 17, Solvent Red 23, Ceresin Red) is very water insoluble but soluble in sesame oil, a well known oil for parenteral oil-in-water emulsions (e.g. Intralipid, Liposyn, etc.) and has a maximum wavelength of light absorption of 507 nm. Thus, an emulsion of Sudan III was prepared as follows: A saturated solution of Sudan III in sesame oil was prepared by gently rotating the container over a weekend (approx 72 hr). The oil solution was then filtered through a 5 micron syringe filter followed by a 0.8 micron filter to remove undissolved solid Sudan III. The resulting saturated solution was then emulsified in water at a ratio of 10% "oil" to 90% aqueous surfactant solution using ultrasonic energy followed by micro-fluidization at approx 14,000 PSI until a constant droplet size was achieved. Droplet size was measured by light scattering using a Horiba 910 light scattering device and a volume weighted average. The resulting emulsions were also sterilized by traditional steam sterilization and the droplet size measured again with the following results:

| Formulation | Average Droplet Size (nm) | |
|---|---|---|
| | Before Autoclaving | After Autoclaving |
| 1. 1.2% lecithin, 0.3% F68 | 787 | 909 |
| 2. 1.2% lecithin, 2% P79 | 141 | 199 |
| 3. 0.8% lecithin, 3% P79 | 122 | 128 |

P79, described in Example 2 k of PCT/GB95/02109, is a PEG-double ester of molecular weight about 10,000 and formula $CH_3(CH_2)_{13}COO(CH_2)_{15}COO((CH_2)_2O)_{11}CH_3$. P79 is a polymeric surfactant which appears to add greatly to the ability to make a small emulsion droplet of sesame oil saturated with Sudan III. The resulting rose coloured emulsion is stable on the shelf.

During acousto-optic imaging partial breakup of the emulsified particles in regions of strong ultrasound irradiation will increase contact between the dye molecules and water, and the optical properties of the dyes will be altered. This will affect passage of light through the regions of high dye content and high ultrasound irradiation, and contrast in the acousto-optic image between the regions of high and low dye content will be enhanced.

EXAMPLE 11

Formulation of Liposome Stabilized Air Bubbles for Sonoluminescence

A liposome suspension was formed from 8.2% lecithin (phosphatidyl choline), 0.8% dimyristalphosphatidylglycerol, and 0.1% of a nonionic, polymeric surfactant, P-79, which is designed to impart prolonged blood pool residence to the liposome. The phospholipids and the surfactant were mixed in water using ultrasonic energy from a probe sonicator (Bransonic Sonifier 450, 90% duty cycle, output 10). Liposomes were prepared using a Microfluidics M110S microfluidizer at 14,000 PSI and 4 passes through the interaction chamber of the phospholipid mixture. The resulting liposomes were approximately 100 nm in average diameter as determined by light scattering and remained the same size after autoclave sterilization. In addition, these liposomes were able to pass through a sterile filter (i.e. 0.2 micron pore size). The resulting liposomal suspension was freeze dried to yield a white cake in the bottom of a flask. While recovery was carried out under room air, release of the vacuum from the lyophilization process could be carried out under any gaseous atmosphere desired (i.e. nitrogen, xenon, helium, etc.). The recovered vials were capped and stored in the dark at 5° C. until used.

Reconstitution with water for injection resulted in liposomes having air bubbles entrapped within the phospholipid membranae for some time. This suspension could be injected into an animal or human followed by ultrasound irradiation which would activate the bubbles for the sonoluminescent effect. The biodistribution of these air-filled liposomes is governed by the surface coating which in this case is nonionic and able to "hide", the liposomes from the MPS cells.

These particles will be especially useful for sonoluminescence imaging. Only that part of the vasculature actually containing the liposomes will afford a sonoluminescence signal.

EXAMPLE 12

Liposomal Suspension of Entrapped Air Bubbles Stabilized During Freeze Drying by an X-ray Absorbing Dye For Sonoluminescence Imaging Liposomes (CTP-10) of phosphatidyl choline and phosphatidyl serine in a molar ratio of 10 to 1 were prepared by extrusion through stacked 1 micron pore size filters under pressure. These liposomes were prepared in a solution which contained 400 mg/ml iodixanol, an iodinated, soluble X-ray contrast agent. Thus, each liposome contained a significant amount of iodinated contrast agent within the internal aqueous pool of the liposome. This formulation of liposome encapsulated CT X-ray contrast agent (i.e. iodixanol) was administered to rabbits as a single bolus of 150 mg iodine/kg, a divided bolus of 2×75 mg iodine/kg, and a 10 minute infusion of 80 mg I/minute (total dose=800 mg or I approximately 265 mg iodine/kg at 1 ml/min). X-ray imaging was carried out on a GE spiral CT scanner at Paol Verans Hospital, Palo Alto, Calif. Neither the single bolus nor the divide bolus afforded significant blood opacification beyond 1 minute past administration. The infusion, however, provides useful opacification of the blood during the infusion as well as liver enhancement. Even at 5 minutes into the infusion, the contrast in the aorta is approximately 125 HU, at least 50 HU above background opacification levels.

The CT data clearly show the levels of contrast agent present within the various structures (i.e., liver, blood). The current wisdom in the field is that every 30 HU is approximately 1 mg/g of iodine or more approximately 2 mg contrast agent/g of tissue. Thus, contrast agent levels up to 8 to 10 mg/g tissue are achieved in the above dosing regimens.

These liposomes can be freeze dried and stored at 5° C. until use. Upon reconstitution with water for injection, these liposomes will be easily resuspended with air bubbles entrapped within the liposome pools. Upon irradiation with ultrasound, these bubbles will produce a sonoluminescence effect.

EXAMPLE 13

Preparation of a Stable Emulsion of Perfluorobutane, a Gas Bubble Precursor

Perfluorobutane is very water-insoluble but is soluble in sesame oil, a well known oil for parenteral oil-in-water emulsions (e.g. Intralipid, Liposyn, etc.). Thus, an emulsion of perfluorobutane was prepared as follows: A saturated solution of perfluorobutane in sesame oil was prepared by gently rotating the container over a weekend (approx 72 hr). The oil solution was then filtered through a 5 micron syringe filter followed by a 0.8 micron filter to remove any unwanted solid particles. The resulting saturated solution was then emulsified in water at a ratio of 10% "oil" to 90% aqueous surfactant solution (i.e. lecithin, or lecithin+P79) using ultrasonic energy followed by microfluidization at approx 14,000 PSI until a constant droplet size was achieved. Droplet size was measured by light scattering using a Horiba 910 light scattering device and a volume weighted average.

P79, described in Example 2 k of PCT/GB95/02109, is a PEG-double ester of molecular weight about 10000 and formula $CH_3(CH_2)_{13}COO(CH_2)_{15}COO((CH_2)_2O)_{11}CH_3$. P79 is a polymeric surfactant which appears to add greatly to the ability to make a small emulsion droplet of sesame oil saturated with perfluorobutane. The resulting emulsion is stable on the shelf at room temperature.

It is expected that upon injection into the body, the perfluorocarbon gas will be above the vaporization temperature and will thus form gas bubbles within the oil droplets within the vasculature. These gas bubbles will be capable of sonoluminescence upon ultrasound irradiation at various locations within the body, dependant upon the surface character of the oil droplets. With the addition of P79, these droplets will circulate for some time thus affording sonoluminescence from the vasculature which is irradiated with the ultrasound signal. Other emulsion droplets may target various body tissues such as the liver, the spleen, the brain, etc. Irradiation of specific tissues with ultrasound may well afford the sonoluminescent effect.

EXAMPLE 14

Sonoluminescence from Air Bubbles Entrapped in a Porous Solid Particle

Particles of porous, solid iodinated X-ray contrast agents as disclosed in U.S. Pat. No. 5,741,522 (Violante et al, Apr. 21, 1998) would also be useful for sonoluminescence if they retain the gas within the pores for some time post injection. Thus, it is envisioned that these particles can be prepared, freeze dried, reconstituted and injected into the body to afford particles within the vasculature or targeted to a specific tissue which upon irradiation with ultrasound would afford the sonoluminescent effect. This material could also be used in acousto-optical imaging.

EXAMPLE 15

Gas-Filled Microparticles (A)

A microbubble suspension filled with a mixture of 90% nitrogen and 10% xenon, with particle size 1 to 12 $\mu$m, may be prepared with oleic acid and human serum albumin as the microbubble shell material.

A 216 ml sample of a 0.5% aqueous solution of sodium oleate is titrated with 0.1 N HCl so that the final pH is in the range 3.9 to 4.0. The solution becomes very turbid due to the formation of an oleic acid suspension. The particle size as measured by optical microscopy will be in the 0.1 $\mu$m range.

The suspension is pressurized to increase the solubility of the gas in the oleic acid suspension. The suspension is placed in a 500 ml stirred autoclave (Zipperclave manufactured by Autoclave Engineers, Inc.) fitted with a 6-blade turbine-type impeller (Dispersimax). The vessel is sealed and charged to 1000 psig with the nitrogen/xenon gas mixture. The suspensions agitated at 1000 rpm for one hour at room temperature (23–25° C.). Agitation is stopped, the vessel is vented, and the suspension is held for 30 minutes before use. A solution of 2 g human serum albumin (HSA) in 6 g water is added to 28 g of water and 20 g of the emulsion described above. The turbid solution is heated to 65° C. while oxygen gas is bubbled in. The solution is then stirred with an Omni Stirrer (homogenizer) for 5 minutes at the mid-range setting. The foamy mixture is poured into a separatory funnel and left to stand for 30 minutes. The liquid is removed from the bottom, and 10 ml of fresh 1% HSA solution is added to the foam. After 30 minutes the liquid is removed and 10 ml fresh 5% HSA solution is added so that the foam is resuspended into solution. The liquid is quickly collected from the bottom.

EXAMPLE 16

Gas-Filled Microparticles (B)

Encapsulated gas microspheres may be prepared according to WO-A-95/01187 by mixing an aqueous solution of human serum albumin with a gas mixture of 90% nitrogen and 10% xenon.

The recommended dose for imaging is 10 to 200 µl/kg of the liquid for resuspended particles.

EXAMPLE 17

Sonoluminescence Imaging

Sonoluminescence in the flank of a laboratory rat is detected in the manner of Leighton et al., (Ultrasonics, 1990, 28, 181) with a red-sensitive photomultiplier tube (EMI 9658R), which is operated at −20° C. to reduce noise. The output from the photomultiplier is quantified by a 5C1 photon-counting system and a 5C14 pulse-height analyser (EG&G Brookdeal Electronics Ltd). A beam of 1 MHz continues wave ultrasound is generated at powers of up to 2 W/cm by a Therasonic 1030 (Electro Medical Supplies) ultrasound source.

Sonoluminescence is measured before intravenous injection of contrast agent to provide an experimental baseline. The contrast agent is then injected into the tail vein of the rat and sonoluminescence is remeasured within 10 minutes of injection. The preparation of suitable contrast agents for sonoluminescence imaging is described in Examples 1, 2, 4–7 and 11–16 above. Other contrast agents suitable for use in sonoluminescence are described in Examples 5–7 of our copending PCT patent application No. PCT/GB98/01245 entitled "Method of Demarcating Tissue" filed Apr. 29, 1998, the contents of which are incorporated herein by reference.

EXAMPLE 18

Acousto-Optic Imaging

Acousto-optic imaging of tumors implanted in nude mice is done by the procedure of Marks et al. (SPIE, vol. 1888, p. 500). A suitable cell line is HT-29. The implanted tumors are allowed to grow for about 4 weeks before examination.

A remote VIS-NIR model 260 Guided Wave Spectrophotometer is used in conjunction with a 7:7 bundle fiber reflectance probe in the optical studies of the tumors. Reflectance spectra are recorded over the wavelength range 350–1000 nm in 1 nm steps. The reflectance probe delivers ca. 9 mW white light to the tumors through seven fibres. The reflected light is collected with seven additional fibers and is passed through a monochromator with an 0.5 mm slit to a silicon detector. The diameter of the fiber bundle should be 2 m or less.

Optical reflectance is measured by pressing the probe against the tumors with a firm pressure. A base-line measurement is made prior to the injection of contrast agent. The agent is then injected into a tail vein, and the signal is rerecorded. The signal is monitored for up to two hours following injection. The preparation of suitable contrast agents for acousto-optic imaging is described in Examples 1–10 and 14–16 above. Other contrast agents suitable for use in acousto-optic imaging are described in Examples 1–4, 9–23, 26–34, 36–41, 43 and 44 of our copending PCT patent application NO. PCT/GB98/01245 entitled "Method of Demarcating Tissue" filed Apr. 29, 1998, the contents of which are incorporated herein by reference.

What is claimed is:

1. An acousto-optical method of generating information from an animate human or non-human animal body which method comprises:

administering to said body a physiologically tolerable material capable of absorbing, scattering or emitting light at a wavelength in the range 300 to 1300 nm;

subjecting at least a portion of said body to ultrasound irradiation;

if the said material is not sonoluminescent, subjecting at least said portion of said body to light in the wavelength range 300 to 1300 nm;

detecting light in the wavelength range 300 to 1300 nm from said portion of said body, wherein said detected light carries a record of the interaction of the ultrasound on said body; and manipulating the detected light to generate said information.

2. A method as claimed in claim 1 wherein the wavelength of any of said light is in the range of 600 to 1300 nm.

3. A method as claimed in claim 1 wherein the physiologically tolerable material is a soluble dye enclosed in a liposome, whereby under the influence of said ultrasound the liposomes break and reform so as to release dye selectively at the said portion of said body.

4. A method as claimed in claim 1 wherein the physiologically tolerable material is a precursor of a coloured free radical, which precursor is capable of combining with any free radicals produced under the influence of said ultrasound to generate optically detectable markers at said portion of said body.

* * * * *